United States Patent [19]
Grünenfelder et al.

[11] Patent Number: 5,788,485
[45] Date of Patent: Aug. 4, 1998

[54] KILN FOR CERAMIC DENTAL COMPOSITION WITH A PIVOTALLY CONNECTED BEARING ARRANGEMENT

[75] Inventors: Robert Grünenfelder, Vaduz; Jürgen Mertins, Gams; Horst Ulbricht, Eschen, all of Switzerland

[73] Assignee: Ivoclar AG, Liechtenstein

[21] Appl. No.: 749,605

[22] Filed: Nov. 18, 1996

[30] Foreign Application Priority Data

Nov. 17, 1995 [DE] Germany ............... 195 42 984.2

[51] Int. Cl.⁶ .................................................. F27D 1/18
[52] U.S. Cl. .................................. 432/250; 432/206
[58] Field of Search .......................... 432/184, 250, 432/258, 206

[56] References Cited

U.S. PATENT DOCUMENTS 4,139,341  2/1979  Pfaffenbauer ............... 432/184

FOREIGN PATENT DOCUMENTS 26 32 846  4/1978  Germany.
25 43 175  1/1980  Germany.

*Primary Examiner*—Teresa J. Walberg
*Assistant Examiner*—Gregory A. Wilson
*Attorney, Agent, or Firm*—John C. Thompson; Alan S. Korman

[57] ABSTRACT

A kiln has a bottom part with a support for goods to be fired and a top part with a firing chamber. A bearing arrangement including at least one pivot joint pivotably connects the bottom part and the top part. The bearing arrangement includes a lift bearing cooperating with the at least one pivot joint.

17 Claims, 4 Drawing Sheets

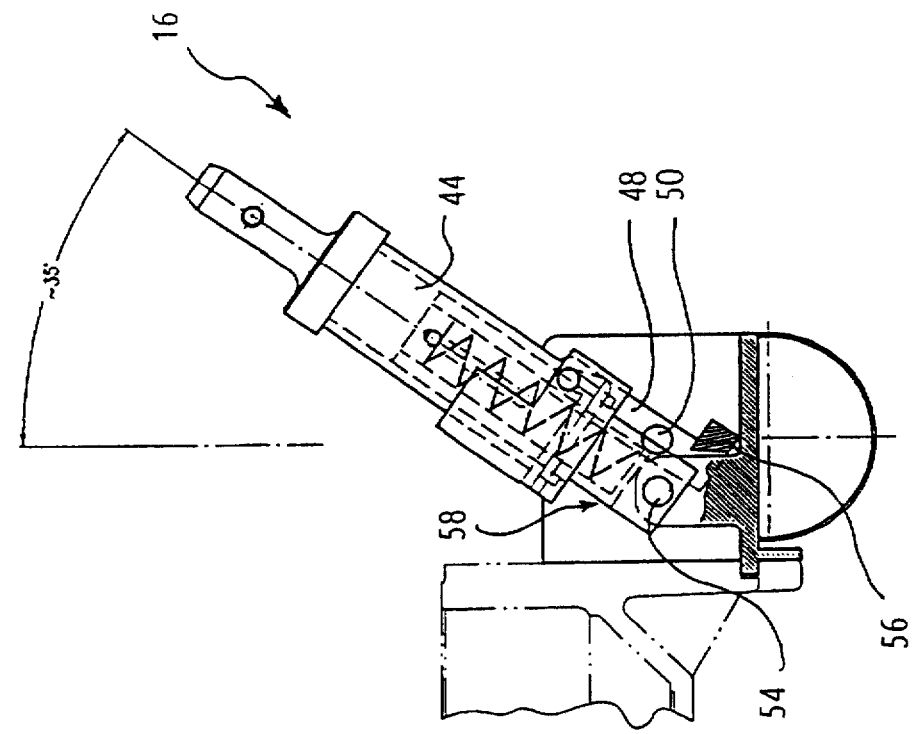
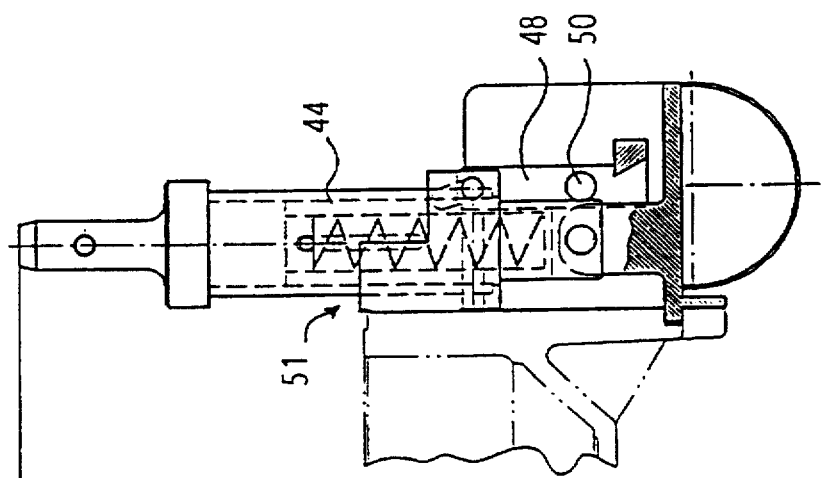
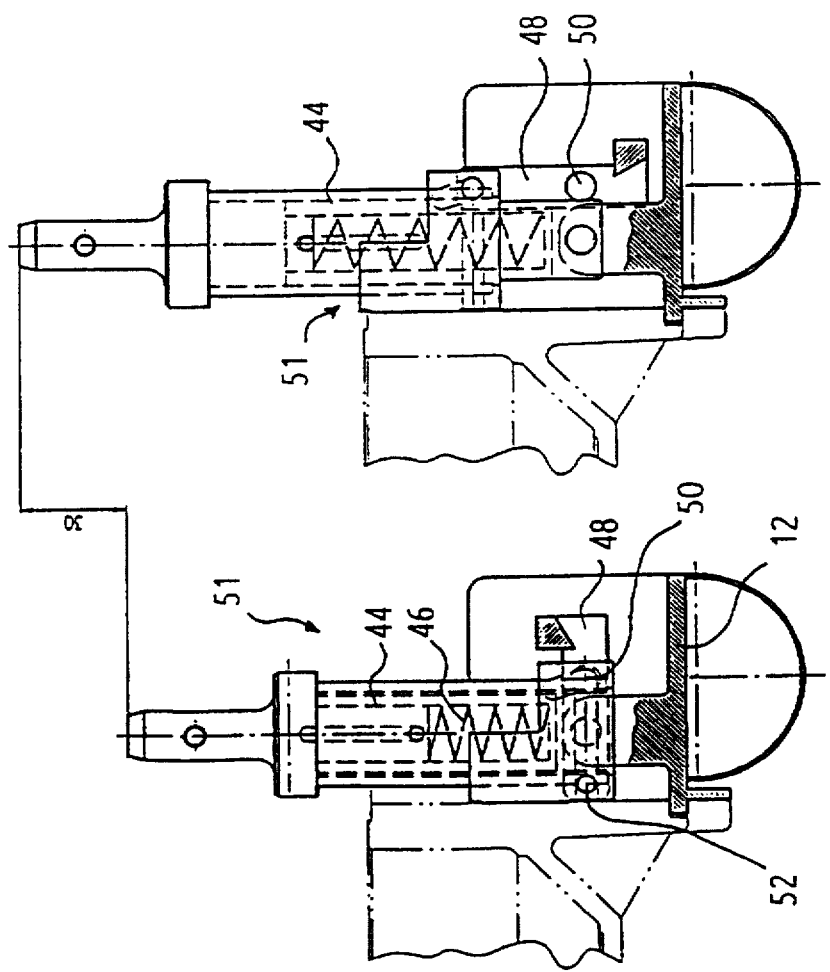

KILN FOR CERAMIC DENTAL COMPOSITION WITH A PIVOTALLY CONNECTED BEARING ARRANGEMENT

This application claims priority from German application 195 42 984.2 filed Nov. 17, 1995.

BACKGROUND OF THE INVENTION

The present invention relates to a kiln, especially for ceramic dental compositions, with a bottom part with a support for the goods to be fired and a top part with a firing chamber which is connected to the bottom part with a bearing arrangement that comprises at least one pivot joint for pivotably supporting the top part at the bottom part.

Such a kiln, for example, is known from German Patent 26 32 846. This kiln has the advantage that it is of a comparatively simple construction and is also easy to handle. Despite its simple design, this kiln has been proven successful over the past decades for firing of different ceramic dental composition.

Furthermore, for a couple of decades kilns have been known in which the top part can be vertically raised. Such an embodiment is known from German Published Document 25 43 175. Such kilns provided with support columns have the disadvantage that the top part must be lifted to a great extent in order to allow for free access to the fired goods. This causes a high center of gravity of the kiln when opened whereby, for reasons of occupational safety, it is required to provide a sufficiently large support surface area which makes the entire kiln unmanageable and which results in low acceptance in dental laboratories.

Also, with respect to ergonomic considerations, the support columns at the kiln are unfavorable because the operator can not easily detect whether the top part provided with heating elements is still glowing red or has already cooled. Due to the spacing from the top part it would be required to provide mirrors for the detection of red heat which mirrors, however, would have to be temperature-resistant; this would be a further disadvantage relative to the pivoting kilns as known, for example, from German Patent 26 32 846. Due to the lack of instant recognition there is also an increased risk for the operator of burning himself.

The kilns of the aforementioned kind are comprised of a bottom part with a substantially plane surface and a top part that comprises the heating elements and thus the actual firing chamber. During opening of the kiln with a pivoting movement, the rear portion of the top part remains in direct vicinity of the top part so that this rear portion, even after a cool-down phase, is still relatively hot while the forward portion cools quickly. This results in a correspondingly uneven cooling of the muffle used for the goods to be fired so that for the unexperienced operator there is a risk of receiving burns because he assumes that the entire muffle has already cooled since the forward portion is cool.

It is therefore an object of the present invention to provide a kiln of the aforementioned kind which with respect to manipulation is improved, provides for a fast and/or uniform cooling of the fired goods without having the top part cool to quickly, and still provides a simple manufacture with excellent acceptance by the customer.

SUMMARY OF THE INVENTION

The inventive kiln is primarily characterized by:
a bottom part with a support for goods to be fired;
a top part with a firing chambers;
a bearing arrangement comprising at least one pivot joint pivotably connecting the bottom part and top part;
the bearing arrangement further comprising a lift bearing cooperating with the at least one pivot joint.

Preferably, the kiln further comprises a control device for sequentially controlling, when opening the kiln, first the lift bearing and subsequently the at least one pivot joint.

The lifting movement of the lift bearing for lifting the top part relative to the bottom part is much smaller than a movement required for completely opening the kiln.

The lifting movement has preferably a range of 10 to 15 millimeter; most preferred the lifting movement is 30 millimeter.

The at least one pivot joint comprises abutments for limiting a pivoting movement of the top part relative to the bottom part.

The pivoting movement comprises a range of 35° for pivoting the top part from a horizontal position into a slanted position.

The control device comprises a drive unit for lifting the top part.

The drive unit, after lifting the top part, pivots the top part.

Advantageously, the control device comprises a drive unit for pivoting the top part.

The control device comprises an electric motor and a cam control, wherein the cam control upon actuating the electric motor first lifts the top part and subsequently pivots the top part.

The bearing arrangement comprises at least one spring acting on the pivot joint for substantially compensating the weight of the top part.

The bearing arrangement comprises at least one spring acting on the pivot joint and the lift bearing for substantially compensating the weight of the top part.

The bearing arrangement may comprise at least one spring acting on the lift bearing for substantially compensating the weight of the top part.

The bottom part has an upper surface. The kiln may further comprise storage shelves connected laterally to the upper surface of the bottom part so as to be flush with a contour of the upper surface.

The storage shelves consist of a heat-absorbing material.

The control device comprises a keyboard pivotably connected to a front side of the bottom part, wherein the keyboard is pivotable about a pivoting range including a pivot position in which the keyboard is positioned at a right angle to the underside of the top part when lifted and pivoted.

The inventive kiln has the surprising advantage that, despite the pivoted position of the top part in the open position of the kiln, the muffle or the fired goods will cool surprisingly uniformly and quickly so that the risk of getting burned for an unexperienced operator is greatly reduced. Apparently, due to the rearward portion of the top part which is also slightly lifted by the lift bearing, an especially favorable air flow between the top part and the bottom part, i.e., the gap extending therebetween, is produced which favors the cooling process. With respect to the air flow it is furthermore favorable in regard to flow-technological aspects, that the firing chamber of the top part is still rather hot so that below the firing chamber, due to the air rising from there, a vacuum results which improves the air flow. Due to the air flow, the cooling process is shortened so that the top part cools to a lesser degree.

Surprisingly, a gap of, for example, 30 mm is already sufficient to produce the desired effect. However, it is understood that the lifting movement can be adjusted within wide ranges to the specific requirements. The cam control required for the combined movement is either provided by exchanging the corresponding cam plate with the control contour or by supporting the bottom part such, inasmuch as it concerns the support for the goods to be fired, that it is vertically downwardly moveable.

In an alternative embodiment of the invention it is suggested to support the top part so as to be pivotable and to lower the bottom part via the lift bearing so that the desired gap will be provided. The movements can be controlled by one single control device.

It is especially advantageous that with the pivoting movement in connection with the vertical movement the center of gravity is maintained at a relatively low level so that even for a support surface area which is within the size limits of the bottom part the risk for tipping over is only minimal.

According to another advantageous embodiment lateral support surfaces are provided at the bottom part. They do not impede the air flow and can simplify manipulation substantially since it is possible to move the fired goods quickly onto the support surfaces and to introduce immediately the next charge of goods to be fired onto the support surface of the firing chamber so that the kiln can be started up again without delay.

The control device can be manually operated whereby it is favorable that the weight of the top part be at least partially compensated by at least one spring. Then, an easy manipulation of the top part is possible, and, furthermore, a catch in the upper open position of the kiln and, if needed, also a closure in the closed position, i.e., the firing position of the kiln, can be realized.

According to another advantageous use of the inventive kiln, the lifting movement can be used for defining certain firing cycles. For example, the top part can be first lifted vertically in order to ensure a uniform pre-drying of the goods to be fired and the insulation bricks (refractive material). When a uniform cooling is important, the goods that have been fired can be first left within the kiln in the position of maximum lift. Depending on the goods that have been fired, respectively, their material properties, a directed slow or quick cooling process can be performed whereby it is understood that the lifting movement can be controlled via the control device and a corresponding program. For example, individual pre-drying processes can be realized by varying the lift of the lifting movement. For example, a lifting movement to only half of the maximal lift results in a correspondingly slowed cooling process.

However, the lifting and pivoting movements can be easily controlled. In one embodiment, a simple work cylinder which is pivotably supported at its bottom is combined with an also movably supported cam disc or plate. As soon as within the contour of the cam disc the follower has reached the upper vertical position, the pivoting movement according to the cam contour is started upon further stretching movement of the work cylinder. Thus, the inventive control can also be realized with only one simple drive. This arrangement further has the advantage that the top part is easily removable which is especially favorable for servicing and repair purposes.

According to another advantageous embodiment, a keyboard is provided which is not integrated into the bottom part of the kiln but is pivotable into a slanted position relative to the bottom part. In this context it is especially favorable that the keyboard can be pivoted such that, for a maximal pivoting movement of the top part, the keyboard is positioned with its upper surface at an angle of 90° to the underside of the top part. In this position the heat radiation of the top part will not heat the keyboard which is favorable with respect to operating the keyboard and with respect to general acceptance by the operator. Furthermore, the operator can position the keyboard according to his requirements, which is favorable with respect to ergonomic considerations but also facilitates reading of a possibly provided display.

BRIEF DESCRIPTION OF THE DRAWINGS

The object and advantages of the present invention will appear more clearly from the following specification in conjunction with the accompanying drawings, in which:

FIGS. 7, 8, and 9 show schematic representations of a work cylinder for actuating the bearing arrangement for the inventive kiln of FIG. 1.

DESCRIPTION OF PREFERRED EMBODIMENTS

The present invention will now be described in detail with the aid of specific embodiments utilizing FIGS. 1 through 9.

Figure 1:
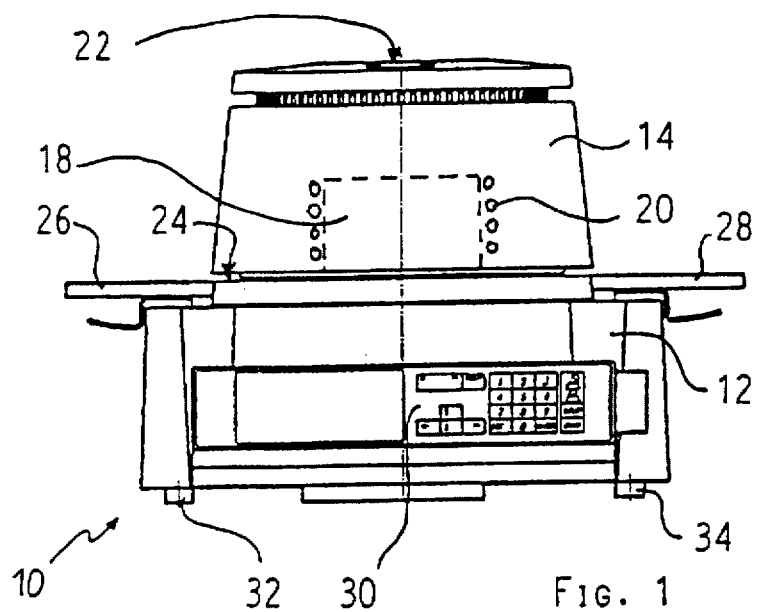
FIG. 1 is a view of one embodiment of the inventive kiln from the front in a closed position of the kiln.

The kiln 10 represented in FIG. 1 comprises a bottom part 12 and a top part 14 which are connected to one another with a bearing arrangement 16. The bottom part 12 comprises a plane surface with integrated support for the goods to be fired which is known per se and does not require a further detailed discussion. The top part 14 comprises a firing chamber 18 provided with heating elements 20 which extend above the support for the goods to be fired.

The top part 14 comprises furthermore a window 22 that allows monitoring of the goods to be fired during the firing process.

Laterally positioned at the upper surface 24 of the bottom part 12 are heat-insulated storage shelves 26 and 28 which serve to temporarily support the goods either before firing or after the firing process for cooling. The design of such storage shelves 26 and 28 can be seen in particular in FIG. 3.

Figure 2:
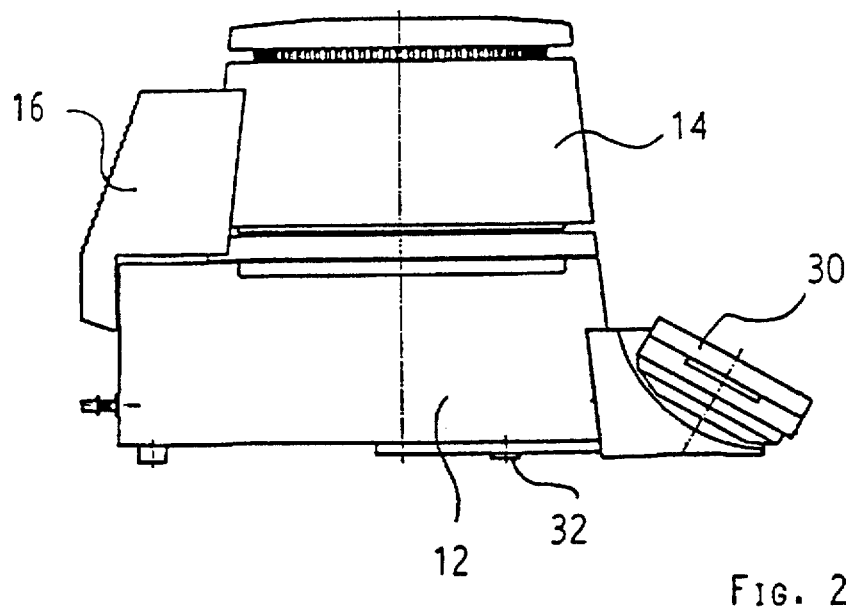
FIG. 2 shows the kiln of the embodiment of FIG. 1 in a side view.

The bottom part 12 further comprises a keyboard which is pivotably supported at a slant as can be seen especially in FIG. 2. Furthermore, the bottom part 12 is provided in a manner known per se with legs, two of which (32, 34) can be seen in FIG. 1. They are positioned at the outer contour in order to provide a secure support of the kiln.

As can be seen in FIG. 2, the bearing arrangement 16 is of a relatively massive construction and provides a secure support for the top part 14. It is possible to embody the bearing arrangement 16 of two spaced-apart bearing brackets which provide, on the one hand, great stability even with respect to lateral loads, and, on the other hand, do not impede the cooling process. The bearing arrangement 16 is furthermore provided with a control device which controls the desired lifting movement and pivoting movement of the top part 14 relative to the bottom part 12 depending on a program input via the keyboard 30.

Figure 3:
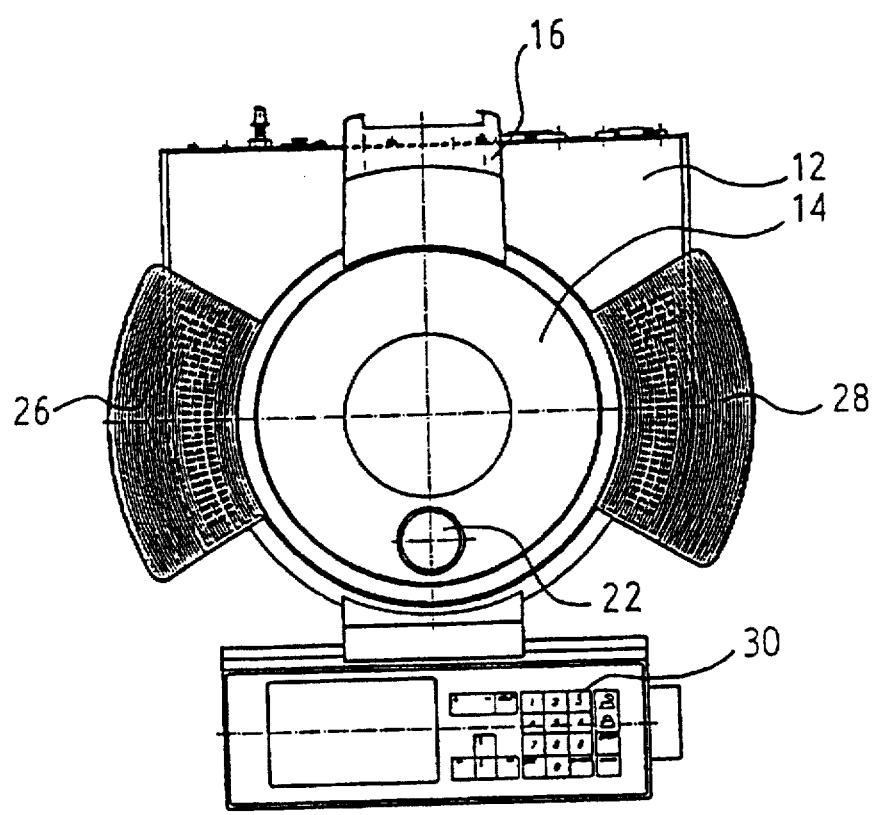
FIG. 3 shows a top view of the kiln of FIG. 1.

As is visible in FIG. 3, the keyboard 30 is spaced from the bottom part 12 but is securely attached thereto so as to form a constructive unit therewith. The thermal separation allows for a more comfortable manipulation whereby due to the pivotability of the keyboard 30, an ergonomically favorable alignment is possible.

As can be seen in FIG. 3, the window 22 is provided at the forward edge of the top part 14 which facilitates viewing of the contents of the kiln by the operator.

Figure 4:
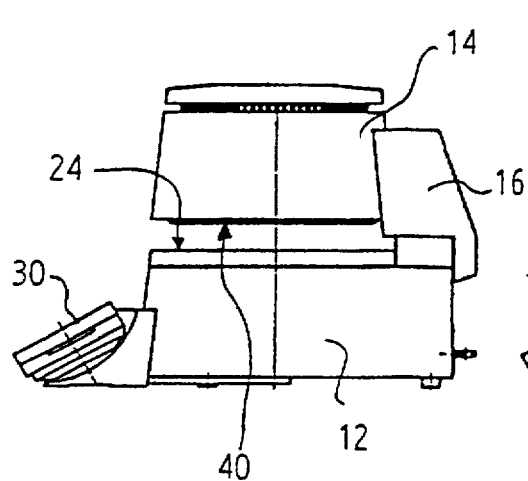
FIG. 4 shows a view of an embodiment of the inventive kiln of FIG. 1 in position of maximal lift.

While the kiln 10 represented in FIGS. 1 to 3 of the shown embodiment is represented in the closed position, FIG. 4 shows the kiln after actuation of the control device for controlling the lift bearing. In this state, the top part 14 extends substantially parallel to the surface 24 of the bottom part 12, but is spaced with its underside 40 therefrom. Depending on the program selected via the keyboard 30, a pre-cooling phase can be preformed in this position which makes it possible that a portion of the non-represented muffle is still within the firing chamber 18 but the other portion is already cooling. If desired, it is thus possible to provide for a slow and uniform cooling of the fired goods.

Figure 5:
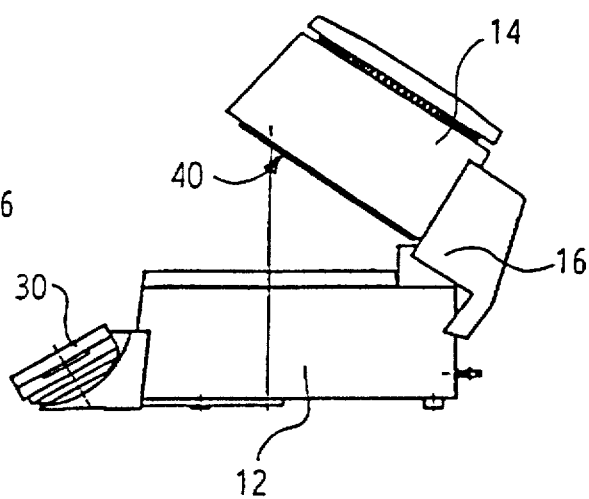
FIG. 5 shows the kiln according to FIG. 1 in the maximum open position.

The position of the kiln represented in FIG. 5 allows for easy access of the fired goods by the operator in the completely open position of the kiln. In this position, the top part 14 is lifted to the maximum extent and is also pivoted to the maximum extent. The fired goods can thus cool quickly especially because the air flow is increased by the still hot firing chamber. The inventive kiln 10 can thus be adjusted within a broad range to the cooling and pre-drying requirements of the employed dental ceramic compositions or other dental materials.

Figure 6:
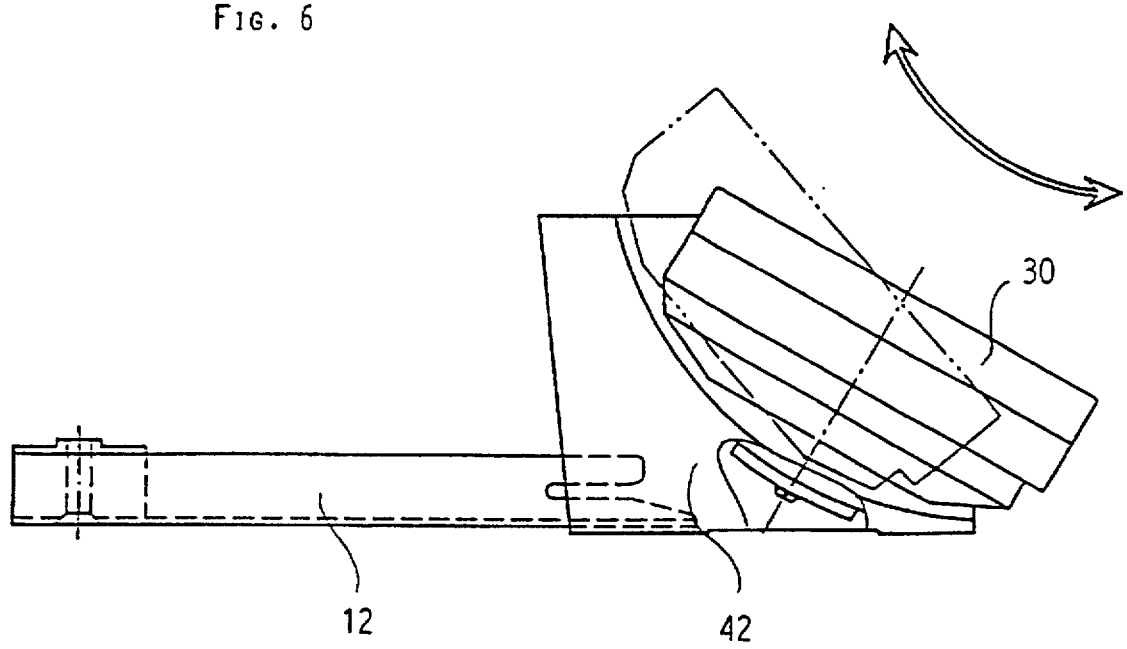
FIG. 6 shows a side view of the pivotable keyboard for the embodiment of FIG. 1 of an inventive kiln.

As can be seen in FIG. 6, the pivotable support of the keyboard is realized in a simple manner. The keyboard comprises a convexly curved backside and a keyboard support 42 with a concave surface whose radius is adapted to the convex backside of the keyboard. The surface has a slot through which a screwed bolt with a securing disc penetrates which is threaded into the back side of the keyboard. In this manner the keyboard is supported at the bottom part with simple means in a reliable manner, ensuring pivotability and spacing.

FIGS. 7 through 9 show a part of the non-represented control device for realizing the inventive bearing arrangement. The work cylinder 44 is represented in the contracted state in FIG. 7 in which a spring 46 is compressed to the maximum extent. A cam disc 48 extends substantially horizontally. It is pivotably supported at a bearing pin 50 and is entrained with a guide pin 52 by the movable part of the work cylinder 44. As can be seen when comparing FIGS. 7 and 8, the control disc 48, upon extension of the work cylinder 44, is pivoted into a vertical position in which a further translatory displacement between the bearing pin 50 and the guide pin 52 is no longer possible. The dimensions are selected such that this work cylinder 44 corresponds to the desired lift of the lift bearing. Thus, the bearing arrangement with these elements provides a lift bearing 51.

A further extension of the work cylinder thus results in that the work cylinder itself, which is pivotably supported in a pivot bearing 54, is laterally pivoted together with the control disc 48. The control disc 48 at its lower end is provided with an abutment 56 which cooperates with the bottom portion 12 and limits the pivoting movement. In the represented embodiment, the pivoting movement corresponds to a pivot range of 35° and the pivot bearing 54 act simultaneously as a pivot joint 58 of the bearing arrangement 16.

It is understood that, by exchanging the control disc 48, the lifting movement of approximately 30 mm as well as the pivoting movement can be adapted within a wide range to any specific requirements.

The present invention is, of course, in no way restricted to the specific disclosure of the specification and drawings, but also encompasses any modifications within the scope of the appended claims.

What is claimed is:

1. A kiln comprising:
   a bottom part with a support for goods to be fired;
   a top part with a firing chamber;
   a bearing arrangement connecting said bottom part and said top part, said bearing arrangement including
   at least one pivot joint pivotally connecting said bottom part and said top part, and
   a lift bearing cooperating with at least said one pivot joint for initially raising the entire top part vertically with respect to the bottom part to facilitate cooling of the top part.

2. A kiln comprising:
   a bottom part with a support for goods to be fired;
   a top part with a firing chamber;
   a bearing arrangement comprising at least one pivot joint pivotally connecting said bottom part and said top part; said bearing arrangement further comprising a lift bearing cooperating with said at least one pivot joint, and
   a control device for sequentially controlling, when opening said kiln, first said lift bearing and subsequently said at least one pivot joint.

3. A kiln according to claim 1, wherein a lifting movement of said lift bearing for lifting said top part relative to said bottom part is much smaller than a movement required for completely opening said kiln.

4. A kiln according to claim 3, wherein said lifting movement has a range of 10 to 50 mm.

5. A kiln according to claim 4, wherein said lifting movement is 30 mm.

6. A kiln comprising:
   a bottom part with a support for goods to be fired;
   a top part with a firing chamber;
   a bearing arrangement comprising at least one pivot joint pivotally connecting said bottom part and said top part; said bearing arrangement further comprising a lift bearing cooperating with said at least one pivot joint, wherein said at least one pivot joint comprises abutments for limiting a pivoting movement of said top part relative to said bottom part.

7. A kiln according to claim 6, wherein said pivoting movement comprises a range of 35° for pivoting said top part from a horizontal position into a slanted position.

8. A kiln according to claim 2, wherein said control device comprises a drive unit for lifting said top part.

9. A kiln according to claim 8, wherein said drive unit, after lifting said top part, pivots said top part.

10. A kiln according to claim 2, wherein said control device comprises a drive unit for pivoting said top part.

11. A kiln according to claim 2, wherein said control device comprises an electric motor and a cam control, wherein said cam control upon actuating of said electric motor first lifts said top part and subsequently pivots said top part.

12. A kiln according to claim 1, wherein said bearing arrangement comprises at least one spring acting on said pivot joint for substantially compensating the weight of said top part.

13. A kiln according to claim 1, wherein said bearing arrangement comprises at least one spring acting on said pivot joint and said lift bearing for substantially compensating the weight of said top part.

14. A kiln according to claim 1, wherein said bearing arrangement comprises at least one spring acting on said lift bearing for substantially compensating the weight of said top part.

15. A kiln comprising:
- a bottom part with a support for goods to be fired;
- a top part with a firing chamber;
- a bearing arrangement comprising at least one pivot joint pivotally connecting said bottom part and said top part;

said bearing arrangement further comprising a lift bearing cooperating with said at least one pivot joint, wherein said bottom part has an upper surface, said kiln further comprising storage shelves connected laterally to an upper surface of said bottom part so as to be flush with a contour of said upper surface.

16. A kiln according to claim 15, wherein said storage shelves consist of a heat-absorbing material.

17. A kiln according to claim 2, wherein said control device comprises a keyboard pivotably connected to a front side of said bottom part, wherein said keyboard is pivotable about a pivoting range including a pivot position in which said keyboard is positioned at a right angle to an underside of said top part when lifted and pivoted.

* * * * *